United States Patent
Fayad et al.

(10) Patent No.: US 7,369,887 B2
(45) Date of Patent: May 6, 2008

(54) RAPID MULTISLICE BLACK BLOOD DOUBLE-INVERSION RECOVERY TECHNIQUE FOR BLOOD VESSEL IMAGING

(75) Inventors: Zahi A. Fayad, New York, NY (US); Vitalii V. Itskovich, Brooklyn, NY (US); Venkatesh Mani, Rockaway, NJ (US); Michael M. Szimtenings, Astoria, NY (US)

(73) Assignees: Mount Sinai School of Medicine, New York, NY (US); Siemens Medical Solutions USA, Inc., Malvern, PA (US)

( * ) Notice: Subject to any disclaimer, the term of this patent is extended or adjusted under 35 U.S.C. 154(b) by 399 days.

(21) Appl. No.: 10/606,665

(22) Filed: Jun. 26, 2003

(65) Prior Publication Data

US 2005/0010104 A1    Jan. 13, 2005

(51) Int. Cl.
*A61B 5/05* (2006.01)
(52) U.S. Cl. .................. 600/413; 600/419; 600/428
(58) Field of Classification Search ............... 600/413, 600/428
See application file for complete search history.

(56) References Cited

U.S. PATENT DOCUMENTS

2003/0069493 A1 * 4/2003 Pan et al. .................. 600/410
2004/0181146 A1 * 9/2004 Yarnykh et al. ............. 600/419

OTHER PUBLICATIONS

Edelman et al., "Fast Selective Black Blood MR Imaging," Radiology 181(3):655-60 (1991).
Yarnykh et al., "Feasibility of Multi-Slice Black-Blood Inversion-Recovery Imaging," Proc. Intl. Soc. Mag. Reson. Med. 10 (2002).
Parker et al., "Improved Efficiency in Double-Inversion Fast Spin-Echo Imaging," Mag. Reson. Med. 47(5):1017-1021 (2002).
Song et al., "Multislice Double Inversion Pulse Sequence for Efficient Black-Blood MRI," Mag. Reson. Med. 47(3):616-620 (2002).
Song, "Highly Efficient Double Inversion Spiral Technique for Coronary Vessel Wall Imaging," Proc. Soc. Mag. Reson. Med. 10:1563-1566 (2002).
Fayad et al., "Clinical Imaging of the High-Risk or Vulnerable Atherosclerotic Plaque," Circulation Research 89(4):305-316 (2001).
Nayak et al., "Real-Time Black-Blood MRI Using Spatial Presaturation," J. Magn. Reson. Imaging 13:807-12 (2001).
Simonetti et al., "'Black-Blood' T2-Weighted Inversion Recovery MR Imaging of the Heart," Radiology 199:49-57 (1996).
Yuan et al., "Carotid Atherosclerotic Plaque: Noninvasive MR Characterization and Identification of Vulnerable Lesions," Radiology 221:285-99 (2001).
Yarnykh et al., "Multislice Double Inversion-Recovery Black-Blood Imaging with Simultaneous Slice Reinversion," J. Magn. Reson. Imaging 17:478-83 (2003).
Cai et al, Circulation 106(11):1368-73 (2002).
Yarnykh et al. "Feasibility of multi-slice black-blood double inversion-recovery imaging". Proc. Intl. Soc. Mag. Reson. Med. 10, 2002.
Parker et al. "Improved Efficiency in Double-Inversion Fast Spin-Echo Imaging". Magnetic Resonance in Medicine 47:1017-1021, 2002.
Edelman et al. "Fast Selective Black Blood MR Imaging". Radiology 181:655-660, 1991.

(Continued)

*Primary Examiner*—Brian L. Casler
*Assistant Examiner*—Parikha S. Mehta
(74) *Attorney, Agent, or Firm*—Fish & Richardson P.C.

(57) ABSTRACT

DIR imaging of blood vessels by administering a series of DIR preparation pulse modules at a repetition interval short enough that at least two DIR preparation pulse modules generally occur within each RR interval, and by acquiring image data for a plurality of slices following each DIR module.

9 Claims, 2 Drawing Sheets

OTHER PUBLICATIONS

Cai et al. "Classification of Human Carotid Atherosclerotic Lesions With In Vivo Multicontrast Magnetic Resonance Imaging". Circulation 106:1368-1373, 2002.

Yuan et al. "Carotid Atherosclerotic Plaque: Noninvasive MR Characterization and Identification of Vulnerable Lesions". Radiology 221(2):285-299, 2001.

Simonetti et al. ""Black Blood" T2-weighted Inversion-Recovery MR Imaging of the Heart". Radiology 199(1):49-57, 1996.

Nayak et al. "Real-time Black-Blood MRI Using Spatial Presaturation". Journal of Magnetic Resonance Imaging 13:807-812, 2001.

Fayad et al. "Clinical Imaging of the High-Risk or Vulnerable Atherosclerotic Plaque". Circulation Research: Journal of the American Heart Association 89(4):305-316, 2001.

Yarnykh et al. "Multislice Double Inversion-Recovery Black-Blood Imaging With Simultaneous Slice Reinversion". Journal of Magnetic Resonance Imaging 17:478-483, 2003.

Song et al. "Multislice Double Inversion Pulse Sequence for Efficient Black-Blood MRI". Magnetic Resonance in Medicine 47:616-621, 2002.

Song et al. "Highly Efficient Double-Inversion Spiral Technique for Coronary Vessel Wall Imaging". Proc. Intl. Soc. Mag. Reson. Med. 10, 2002.

* cited by examiner

RAPID MULTISLICE BLACK BLOOD DOUBLE-INVERSION RECOVERY TECHNIQUE FOR BLOOD VESSEL IMAGING

TECHNICAL FIELD

This invention relates to magnetic resonance imaging of blood vessel walls.

BACKGROUND

Atherosclerosis and its thrombotic complications are the leading cause of morbidity and mortality in developed countries. Non-invasive atherosclerotic plaque assessment using high-resolution magnetic resonance imaging (MRI) has been shown to be feasible in vivo in the human aorta, carotid, and coronary arteries. Flow suppression (i.e., black blood imaging) is necessary for vessel wall visibility and for preventing flow artifacts, which can affect image quality and interpretation. Black blood techniques include spatial pre-saturation (Nayak et al., Real-time black-blood MRI using spatial presaturation, *J Magn Reson Imaging* 2001;13:807-12) and double inversion recovery (DIR) preparation pulse modules (Simonetti et al., "Black-Blood" T2-weighted inversion recovery MR imaging of the heart, *Radiology* 1996;199:49-57).

The DIR preparation pulse modules typically consist of two 180-degree radio frequency (RF) pulses and are applied prior to image acquisition. The first non-selective RF pulse inverts the magnetization of the whole volume. The second selective RF pulse restores the magnetization in ("reinverts") the slice of interest. After a time delay (inversion time, $TI_0$), required for the magnetization of blood to reach the null point, the imaging slice is acquired (Simonetti et al.). The conventional DIR prepared two-dimensional imaging sequence acquires a few lines of k-space from one slice following each DIR module. Acquisition of multiple slices in this fashion results in long experiment times. For example, to acquire 20 slices with 256 lines and turbo factor of 9, a conventional DIR-RARE sequence would take 1160 RR intervals (the interval between two successive R waves of the heart), assuming triggering every other heart beat (repetition interval, TR, equal to two RR intervals). This DIR preparation in combination with a rapid acquisition with relaxation enhancement (RARE) readout has been successfully applied in vivo for vessel wall imaging of different vascular beds. Fayad et al., Clinical imaging of the high-risk or vulnerable atherosclerotic plaque, *Circulation Research* 2001;89:305-316. Yuan et al., Carotid Atherosclerotic Plaque: Noninvasive MR Characterization and Identification of Vulnerable Lesions, *Radiology* 2001; 221:285-99.

Improved DIR sequences to reduce examination time were recently developed. Song et al., Multislice double inversion pulse sequence for efficient black-blood MRI, *Magn Reson Med* 2002;47;616-20. Parker et al., Improved efficiency in double-inversion fast spin-echo imaging, Magn Reson Med, 2002;47:1017-1021. Yarnykh et al., Multislice double inversion-recovery black-blood imaging with simultaneous slice reinversion, J Magn Reson Imaging 2003;17: 478-83.

Song et al. demonstrated a dual-slice DIR technique. The DIR preparation module was modified to include one non-selective and two slice-selective inversion pulses. Following the DIR preparation module, k-space lines from two slices were acquired. A single DIR preparation module was gated to each cardiac cycle (i.e., the repetition interval, TR, was equal to 1 RR interval). Song et al. suggested that data for additional slices could be acquired, but taught that the number of slices possible is limited by the time window during which blood magnetization is nullified. A later publication by Song et al. taught acquiring five slices after each DIR module, using a very short image acquisition sequence, and a DIR repetition interval equal to one RR interval. Song, Highly efficient double-inversion spiral technique for coronary vessel wall imaging, *Proceedings of ISMRM* 2002; 1566.

Parker et al. and Yarnykh et al. taught that improved efficiency could be had by reducing the inversion interval (TI) for nulling the blood signal by administering a repetitive series of DIR modules (FIG. 1*d*) at a repetition interval short enough to put two DIR modules within each RR interval, but both publications taught that only a single slice of image data should be acquired after each DIR module. Parker et al. criticized the multislice technique proposed by Song et al. because "only one of the slices imaged will have the appropriate inversion time to null the signal from blood."

SUMMARY

We have discovered that significantly faster image acquisition can be achieved with DIR imaging of blood vessels by administering a series of DIR preparation pulse modules at a repetition interval short enough that at least two DIR preparation pulse modules generally occur within each RR interval, and by acquiring image data for a plurality of slices following each DIR module. Acquiring image data for a plurality of slices means that image data is acquired at times other than when blood magnetization is perfectly nulled (at exactly $TI_0$), but our research has established that the resulting images have acceptable image quality.

Preferred implementations of the invention may incorporate one or more of the following. The repetition interval for the administered DIR modules may be less than about 500 msec. The inversion time $TI_0$ may be less than about 190 msec. Image data acquisition may extend across an interval that begins before and ends after the inversion time $TI_0$. Image data acquisition may occur in an interval when longitudinal magnetization of blood is reduced to at least 10 percent of full longitudinal magnetization. Image data acquisition may be cardiac triggered or untriggered. The DIR modules may comprise an inversion pulse followed by a reinversion pulse, and the reinversion pulse may reinvert a plurality of the slices to be imaged. The DIR modules may consist of an inversion pulse followed by reinversion pulse that reinverts all of the slices to be imaged. The repetition time (TR) of blood may be disassociated from the TR of the rest of the tissues in the imaging slice.

Other features and advantages of the invention will be apparent from the following detailed description, and from the drawings and claims.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

The descriptions below are more than sufficient for one skilled in the art to construct the disclosed implementations. Unless otherwise mentioned, the processes and manufacturing methods referred to are ones known by those working in the art In a preferred implementation shown in FIGS. 1 and 2, an ECG-triggered pulse sequence is used. The sequence includes two DIR preparation pulse modules within each RR interval, and acquisition of data from three slices (e.g., S11, S12, S13) follows each DIR module. Image acquisition is done using a rapid acquisition with relaxation enhancement (RARE) pulse sequence. Each group of acquisition sequences (e.g., S11, S12, S13) following a DIR module is known herein as a rapid extended coverage (REX) module. The REX module of FIGS. 1 and 2 has three data acquisition sequences for three slices, but other REX modules may acquire data for as few as two slices or for more than three slices.

The DIR module includes two 180-degree adiabatic hyperbolic secant RF pulses: nonselective and selective. The non-selective RF pulse inverts the magnetization of the whole body. The selective 180° pulse is designed to cover a volume that consists of 120% of the entire slab of NSL slices, including inter-slice gaps. The thickness of the slab-selective 180° pulse ($\Delta_{Sel180°}$) was calculated as shown below.

$$\Delta_{sel180°}=(N_{SL}*\Delta_Z+(N_{SL}-1)*\text{Gap})*1.2,$$

where $\Delta_{Sel180°}$ is the thickness of slab-selective 180 degree reinversion pulse, $N_{SL}$ is the number of slices, $\Delta_Z$ is the thickness of each slice, and Gap is the slice separation.

Figure 1:
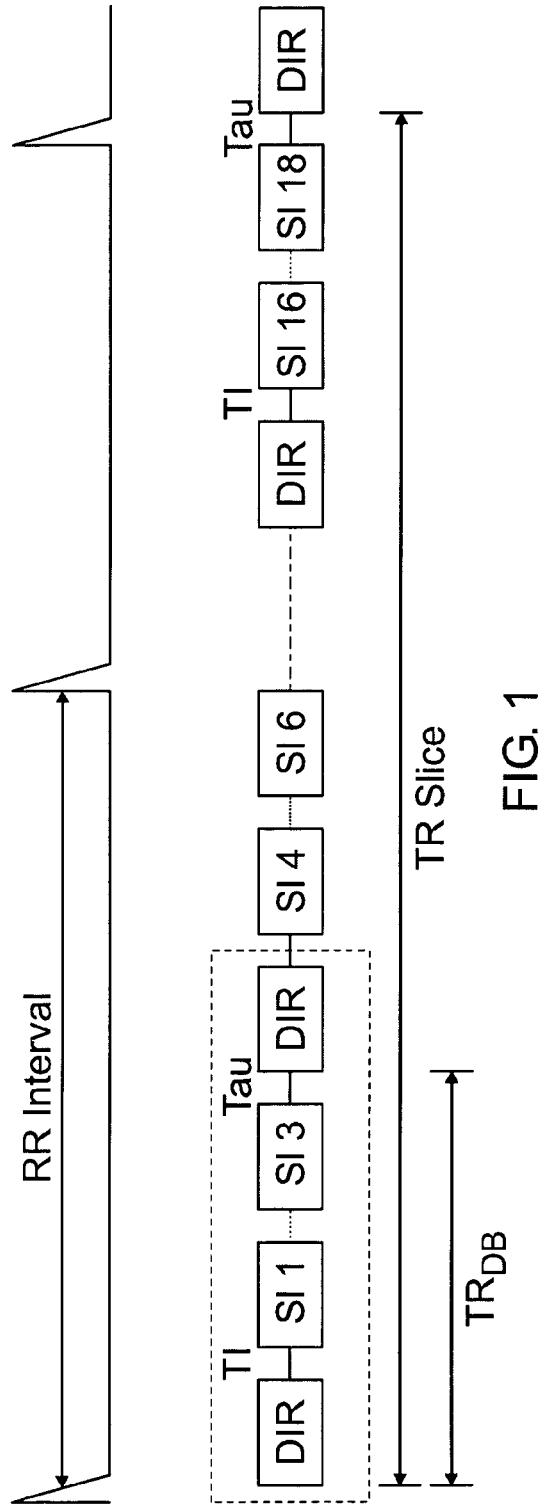
FIG. 1 is a pulse sequence diagram for a preferred implementation of the invention.
Figure 2:
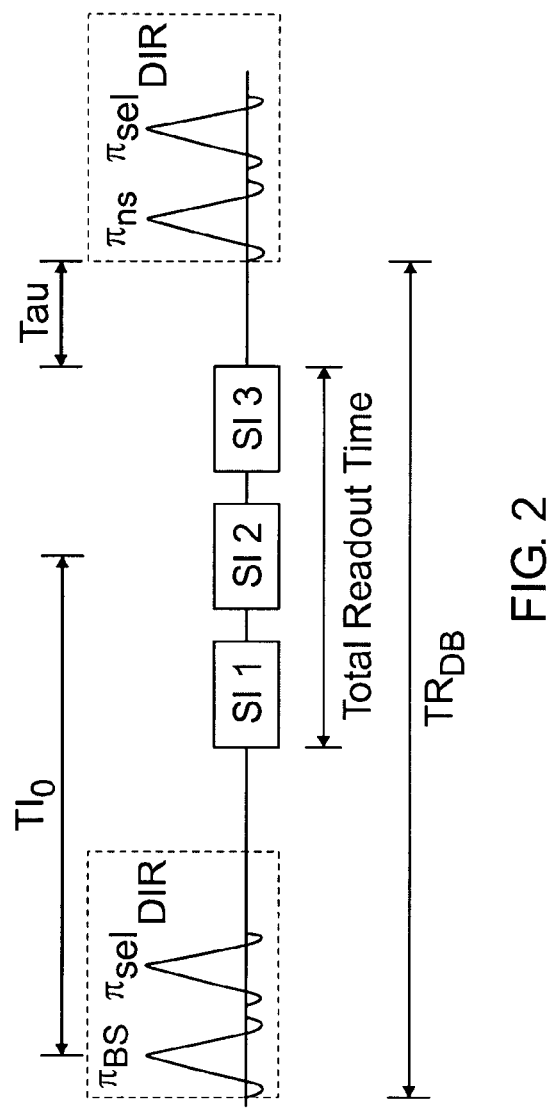
FIG. 2 is an enlarged diagram of one DIR module and associated image acquisition modules of FIG. 1 (the portion of FIG. 1 enclosed by dashed lines).

The sequence acquisition block (REX module) consists of one DIR module followed by multiple (2 to 5) RARE slice readouts. In one implementation, 4-9 REX modules were acquired in 2-RR intervals (the RR interval is the time interval between two consecutive heart beats), yielding 16-20 closely spaced slices. FIG. 1 shows the pulse sequence for 18 slices with 6 REX 3-slice modules. $TI_0$ spans the time from the non-selective RF pulse (inverting the magnetization of the blood) to the middle of the slice readouts in order for them to be as close to the null point of blood as possible.

TR for any slice ($TR_{S1}$) equals 2-RR intervals (typically 1600 ms), and is different from the TR of dark blood ($TR_{DB}$), determined by the time between two successive DIR modules.

$$TR_{DB} = \frac{2RR}{N_{REX}},$$

where $N_{REX}$ is the number of REX modules.

Reduction in $TR_{DB}$ leads to a decrease in dark blood $TI_0$ according to the formula:

$$TI_0=T_1*(ln(2)-ln(1+e^{-TR_{DB}/T_1})),$$

where $T_1$ is the relaxation time of blood (T1=1200 ms at 1.5T).

Figure 3:
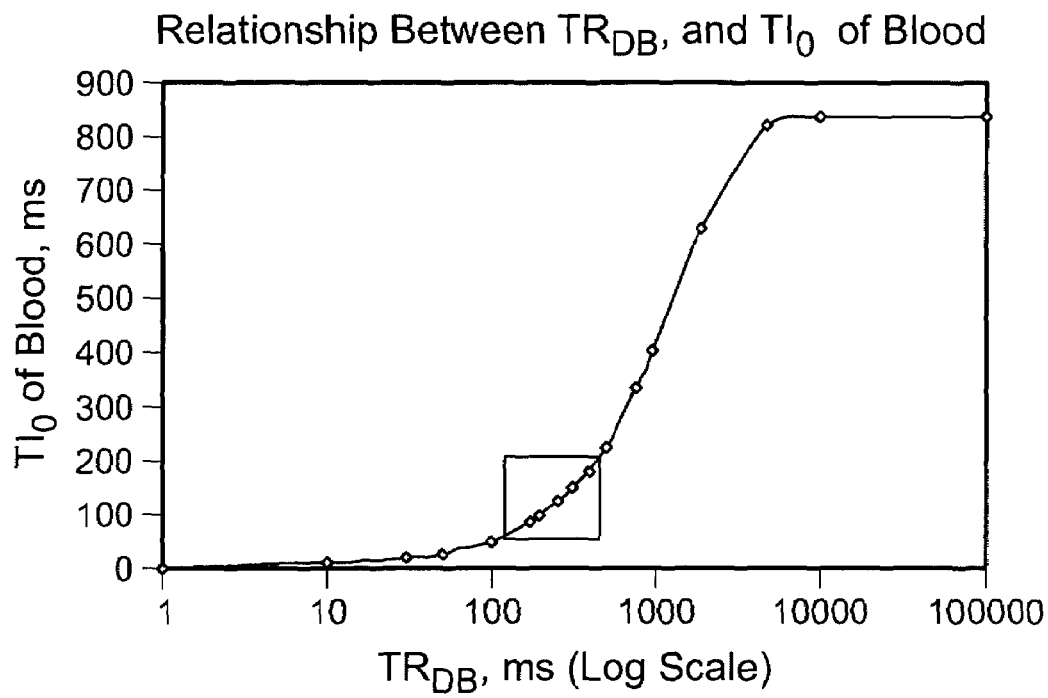
FIG. 3 is a plot showing the relationship between the repetition interval TR of the DIR modules and the inversion time $TI_0$ of blood.

The relationship between $TR_{DB}$ and $TI_0$ of blood, when its signal is nulled is illustrated in FIG. 3. One dummy scan can be performed prior to data acquisition to allow for steady-state inversion recovery.

The fill time between two consecutive REX modules is Tau, as shown by the equation below. Tau (10-50 ms) is added to achieve equal time spacing between REX modules, thereby keeping $TR_{DB}$ constant.

$$Tau=TR_{DB}-(TI_0+T_{DIR}+(0.5+TF)*(N_{SL}*esp)),$$

where $TR_{DB}$ is the TR of dark blood, $TI_0$ is inversion time, $T_{DIR}$ is the duration of the DIR module ($\approx$28 ms), $N_{SL}$ is number of slices, esp is the echo spacing, TF is the turbo factor.

One experiment using the described implementation proceeded as follows: Studies were performed on a 1.5T Siemens Sonata whole body MR system (Siemens AG, Erlangen, Germany) with maximum gradient amplitude of 40 mT/m and slew rate of 200 mT/m/ms running Numaris 4.0. The integrated body coil was used for RF transmission, while a circularly polarized six-channel body array was used for signal reception. Aortic vessel wall MR was performed in 5 healthy adults subjects (aged 27-39 years) without known history of coronary artery disease as approved by the institutional review board. The subjects were positioned headfirst; supine in the magnet bore. Three surface ECG electrodes were placed on the subjects' chest for data acquisition triggering.

Initial scout images in three orthogonal planes were used to locate the descending aorta in the subjects. During aortic wall imaging, the subjects were asked to hold their breath on inspiration when possible. Multislice protocols with 16, 18, and 20 slices were developed. Other imaging parameters were: echo-spacing (esp) of 4.9 ms; echo-time (TE) of 4.9 ms, acquisition matrix size of 256×256, slice thickness of 3 mm, slice separation of 0.3 mm, data acquisition bandwidth of 488 Hz/pixel, one signal average, and a field of view (FOV) of 250 mm were used. The slice excitation order was descending (from head to foot, along the flow direction) for aortic protocols. The slice readout time ($\approx$esp*TF) ranged between 44 and 64 ms. This ensured minimum vessel wall motion and blurring along the phase encoding direction. Turbo factors (9 to 13) were maximized for a given number of slices to fit the readouts within the TR interval.

A variety of REX DIR-RARE implementations of the invention were quantitatively compared to the images of conventional single slice RARE sequence with 16, 18, and 20 slices. The following table summarizes the implementations examined.

| Sequence type | Number of slices/REX modules | Turbo factor | TR of blood (2RR/N$_{REX}$, ms) | TI$_0$ (ms) | Total readout time (ms) | Acquisition time (RR-intervals) |
|---|---|---|---|---|---|---|
| REX multislice DIR-RARE | 16 slices 4 REX modules | 13 | 400 | 183 | 265 | 42 |
| | 16 slices 8 REX modules | 13 | 200 | 96 | 132 | 42 |
| | 18 slices 6 REX modules | 11 | 267 | 126 | 170 | 50 |
| | 18 slices 9 REX modules | 11 | 177 | 85 | 113 | 50 |
| | 20 slices 4 REX modules | 9 | 400 | 183 | 234 | 60 |
| | 20 slices 5 REX modules | 9 | 320 | 149 | 187 | 60 |
| Single slice conventional DIR-RARE (Prior art) | 16 slices | 13 | 1600 | 551 | 67 | 642 |
| | 18 slices | 11 | 1600 | 551 | 57 | 866 |
| | 20 slices | 9 | 1600 | 551 | 47 | 1162 |

In the implementations described in the table, the slice repetition interval, TR, is 2RR intervals. The T1 of blood was assumed to be 1200 msec at 1.5T, and a 2 RR interval was assumed to be 1600 msec. An acquisition matrix of 256×256 was used.

The single slice DIR-RARE sequence consisted of a DIR module followed by acquisition of a single slice in one triggering period (2-RR). The number of slices, as well as other MR imaging parameters of the single slice sequence (2-RR triggering interval, TE, matrix size, slice thickness and separation, bandwidth, FOV, TF) were chosen to be the same as those of the REX multislice sequence in order to equitably compare the quality of the images of both methods.

With DIR imaging techniques, the blood flowing into the imaging plane after the TI$_0$ interval has zero longitudinal magnetization due to the prior application of the non-selective inversion pulse. In the experiment, the slices were acquired along the blood flow direction (from head to foot) to augment outflow effects and hence improve blood suppression. The second slab selective RF pulse in the DIR module reinverted the magnetization of the whole slab of interest (16 to 20 slices), not just the slices imaged after the respective DIR module. This avoided the incomplete recovery of the longitudinal magnetization from the rest of the slices in the imaging slab during the time between two successive DIR modules (e.g., 177 to 400 msec) and resulting loss of muscle signal (SNR).

Typical proton density weighted images from 18 slices in 6 REX 3-slice modules showed flowing blood to appear consistently dark in the descending aorta as shown by the arrows. The image quality and acquisition times for the implementation of the invention (the rapid multislice DIR-RARE sequence) were compared with those for the conventional single slice DIR-RARE. The implementation of the invention demonstrated improved image quality as compared to the single slice sequence. Contrast to noise ratios (CNR) of the implementation were not significantly different from those of single slice DIR-RARE. The speed of the implementation allowed breath hold acquisition for up to 18 slices in healthy volunteers. All 5 healthy subjects held their breath for sequence protocols lasting 45 seconds or less, but breath hold of 45 seconds might not be feasible clinically. However, for the REX sequence the breath hold is optional and is not necessary for successful use. Time improvement factors (ratio between acquisition time of the single slice and corresponding multislice sequences of the implementation of the invention) ranged from 12.25 (16 slice protocol) to 16.54.

The described implementation of the invention separates the TR of the imaging slice from the TR of the blood by introducing multiple DIR modules within 2-RR intervals (TR of slice). The time interval between two successive DIR modules is the TR of blood.

Figure 4:
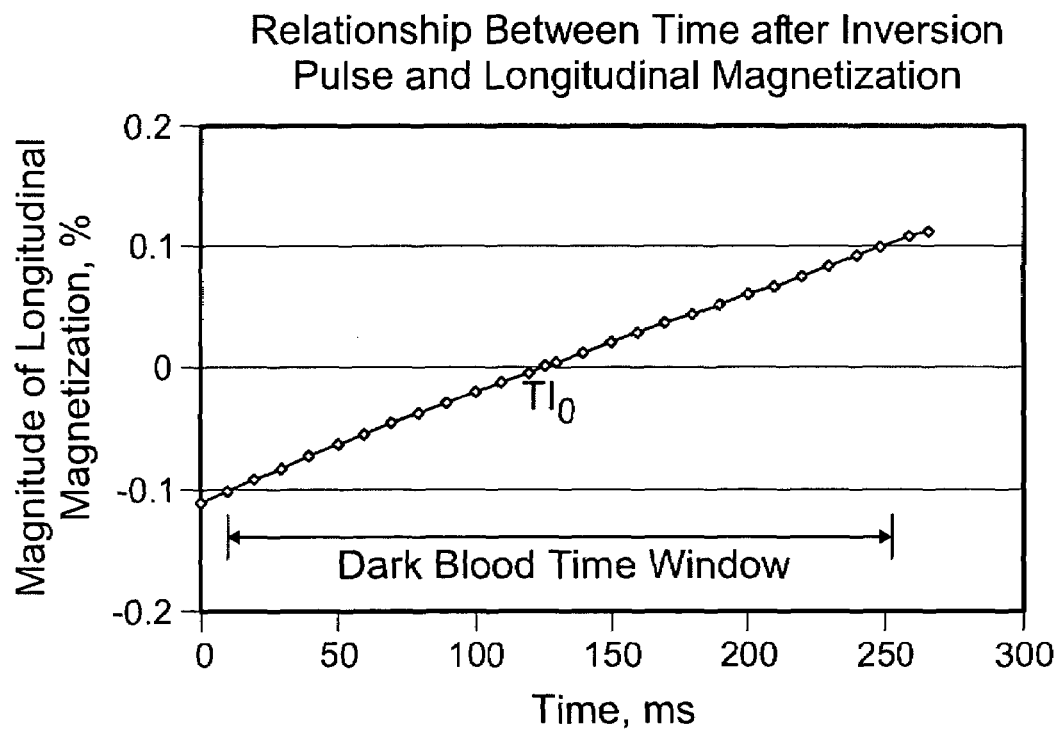
FIG. 4 is a plot showing the relationship between the time after the DIR inversion pulse and the longitudinal magnetization.

In the described implementation, the time window during which the signal from blood is sufficiently suppressed (within 10% of the perfect null point) was approximately 250 msec. FIG. 4 shows the relationship between time after application of the DIR inversion pulse and the longitudinal magnetization of the inverted blood (for a TR$_{DB}$ of 267 msec. The dark blood time window in the figure is the time interval over which blood magnetization is suppressed to 10 percent or less. For the multi-slice implementations described herein, the total readout times ranged from 113 to 265 msec, enabling their acquisition to fit into this time window.

Many other implementations of the invention other than those described above are within the invention, which is defined by the following claims. The following are just a few examples of the many other implementations possible:

Many other image acquisition pulse sequences other than RARE can be used.

We have used the terminology REX module to refer to a DIR module and associated image acquisition sequences. But this is just a choice of terminology, and does not limit the type of DIR module or image acquisition sequence used. Many different DIR modules and many different acquisition sequences could be used within a REX module, and image data for many different numbers of slices can be acquired by one REX module.

Field of view reduction techniques, such as selective presaturation pulses, could be employed with some implementations of the invention, as these techniques could improve the resolution of black blood imaging to a level that would allow vessel wall segmentation.

Three-dimensional (3D) image acquisition could be employed with some implementations. Advantages of 3D acquisition include better excitation slice profile and better SNR. However, any motion, which is not compensated by gating, has the potential to corrupt all slices in the scan, and a wrapping artifact may be present in the Fourier encoded 3D imaging.

Multi-contrast imaging (T1, T2, and PD weighting) is possible with some implementations. For T1-weighted images it may be possible to image up to 10 slices per TR interval. In combination with field of view reduction techniques, more efficient k-space coverage (e.g., spiral readouts, and parallel imaging, it may be possible to image the entire length of the coronary arteries in a single breath hold acquisition.

Other forms of inversion pulses can be used other than the adiabatic secant pulses described. Adiabatic pulses are not necessary. The initial inversion pulse could be the usual hard pulse taught in the literature for DIR imaging.

What is claimed is:

1. A method of magnetic resonance imaging of blood vessel walls, comprising
   administering a series of DIR preparation pulse modules at a repetition interval short enough that at least two DIR preparation pulse modules generally occur within each RR interval;
   in the interval between each DIR preparation pulse module, acquiring image data for a plurality of slices;
   repeating the data acquisition across a plurality of RR intervals to acquire images for the plurality of slices; and
   generating an output based on the images.

2. The method of claim 1 wherein the repetition interval for the administered DIR modules is less than about 500 msec.

3. The method of claim 1 wherein an inversion time $TI_0$ is less than about 190 msec.

4. The method of claim 1 wherein image data acquisition extends across an interval that begins before and ends after the inversion time $TI_0$.

5. The method of claim 4 wherein image data acquisition occurs in an interval when longitudinal magnetization of blood is reduced to at least 10 percent of full longitudinal magnetization.

6. The method of claim 1 wherein image data acquisition is cardiac triggered.

7. The method of claim 1 wherein image data acquisition is untriggered.

8. The method of claim 1 wherein the DIR modules comprises an inversion pulse followed by a reinversion pulse, and the reinversion pulse reinverts a plurality of the slices to be imaged.

9. The method of claim 8 wherein the DIR modules consist of an inversion pulse followed by reinversion pulse that reinverts all of the slices to be imaged.

* * * * *

UNITED STATES PATENT AND TRADEMARK OFFICE
CERTIFICATE OF CORRECTION

PATENT NO. : 7,369,887 B2  Page 1 of 1
APPLICATION NO. : 10/606665
DATED : May 6, 2008
INVENTOR(S) : Zahi A. Fayad et al.

It is certified that error appears in the above-identified patent and that said Letters Patent is hereby corrected as shown below:

Cover Page: Other Publications
Col. 1, Yarnykh et al., reference, After "Black-Blood" insert --Double--.
Col. 2, Song et al., reference, Delete "620" and insert --621--.
Col. 2, Song reference, Delete "Song" and insert --Song et al.,--.
Col. 2, Song reference, Delete "Proc. Soc." and insert --Proc. Intl. Soc.--.
Col. 2, Fayad et al., reference, After "Research" insert --: Journal of the American Heart Association--.
Col. 2, Simonetti et al., reference, Delete "199:49-57" insert --199(1):49-57--.
Col. 2, Yuan et al., reference, Delete "221:285-99" insert --221(2):285-99--.
Col. 2, Delete reference: Yarnykh et al. "Feasibility of multi-slice black-blood double inversion –recovery imaging" (Repeated Entry).
Col. 2, Delete reference: Parker et al., "Improved Efficiency in Double-Inversion Fast Spin-Echo Imaging". (Repeated Entry).
Col. 2, Delete reference: Edelman et al. "Fast Selective Black Blood MR Imaging". (Repeated Entry).

Page 8
Col. 8
Claim 1, Line 5, After "modules" and before "occur" Delete "generally".

Signed and Sealed this

Second Day of September, 2008

JON W. DUDAS
*Director of the United States Patent and Trademark Office*

UNITED STATES PATENT AND TRADEMARK OFFICE
CERTIFICATE OF CORRECTION

PATENT NO. : 7,369,887 B2  
APPLICATION NO. : 10/606665  
DATED : May 6, 2008  
INVENTOR(S) : Zahi A. Fayad et al.

It is certified that error appears in the above-identified patent and that said Letters Patent is hereby corrected as shown below:

Cover Page: Other Publications  
Col. 1, Yarnykh et al., reference, After "Black-Blood" insert --Double--.  
Col. 2, Song et al., reference, Delete "620" and insert --621--.  
Col. 2, Song reference, Delete "Song" and insert --Song et al.,--.  
Col. 2, Song reference, Delete "Proc. Soc." and insert --Proc. Intl. Soc.--.  
Col. 2, Fayad et al., reference, After "Research" insert --: Journal of the American Heart Association--.  
Col. 2, Simonetti et al., reference, Delete "199:49-57" insert --199(1):49-57--.  
Col. 2, Yuan et al., reference, Delete "221:285-99" insert --221(2):285-99--.  
Col. 2, Delete reference: Yarnykh et al. "Feasibility of multi-slice black-blood double inversion –recovery imaging" (Repeated Entry).  
Col. 2, Delete reference: Parker et al., "Improved Efficiency in Double-Inversion Fast Spin-Echo Imaging". (Repeated Entry).  
Col. 2, Delete reference: Edelman et al. "Fast Selective Black Blood MR Imaging". (Repeated Entry).

Page 8  
Col. 8  
Claim 1, Line 11, After "modules" and before "occur" Delete "generally".

This certificate supersedes the Certificate of Correction issued September 2, 2008.

Signed and Sealed this

Thirtieth Day of September, 2008

JON W. DUDAS  
*Director of the United States Patent and Trademark Office*